United States Patent [19]
Heske

[11] Patent Number: 5,546,957
[45] Date of Patent: Aug. 20, 1996

[54] BIOPSY NEEDLE

[75] Inventor: Norbert Heske, Am Brand 1D, 82299 Türkenfeld, Germany

[73] Assignee: Norbert Heske, Terkenfeld County, Germany

[21] Appl. No.: 301,993

[22] Filed: Sep. 9, 1994

[30] Foreign Application Priority Data

Sep. 9, 1993 [DE] Germany ........................ 93 13 569.6

[51] Int. Cl.⁶ ................................................. A61B 10/00
[52] U.S. Cl. ........................ 128/754; 128/751; 128/799
[58] Field of Search .................................. 128/749, 751, 128/753, 754; 604/117, 131, 158, 164, 181, 192

[56] References Cited

U.S. PATENT DOCUMENTS

| | | | |
|---|---|---|---|
| 3,995,619 | 12/1976 | Glatzer .............................. | 128/749 X |
| 4,924,878 | 5/1990 | Nottke ................................ | 128/751 |
| 4,950,265 | 8/1990 | Taylor ................................ | 128/749 X |
| 4,958,625 | 9/1990 | Bates et al. ........................ | 128/749 X |
| 5,172,701 | 12/1992 | Leigh ................................. | 128/753 |
| 5,183,052 | 2/1993 | Terwilliger ........................ | 128/753 |
| 5,188,118 | 2/1993 | Terwilliger ........................ | 128/753 |
| 5,224,470 | 7/1993 | Schnepp-Pesch et al. ........ | 128/753 |
| 5,241,969 | 9/1973 | Carson et al. ..................... | 128/752 |

FOREIGN PATENT DOCUMENTS 536888  4/1993  European Pat. Off. ............... 128/749

*Primary Examiner*—Sam Rimell
*Attorney, Agent, or Firm*—Antonelli, Terry, Stout & Kraus

[57] ABSTRACT

A biopsy system includes a biopsy gun and a biopsy needle, the latter of which has an inner needle, also called a mandrel, and an outer tube, also called a cannula. The mandrel has a recess in the vicinity of its distal end which receives the tissue sample to be collected and has a first collecting element at its proximal end for connection with a slide of the biopsy gun. The cannula also has a connecting element at its proximal end for connection with another slide of the biopsy gun. The connecting elements each have an opening into which a pin provided on each of the respective slides can be inserted. In addition, at least one slide has a rib that extends in the lengthwise direction of the biopsy needle, the rib engaging a corresponding connecting element.

14 Claims, 3 Drawing Sheets

BIOPSY NEEDLE

BACKGROUND OF THE INVENTION

The invention relates to a biopsy needle especially suited for use in a so-called biopsy gun, as well as a biopsy system.

Biopsy needles according to the species are generally known. Mention is made of DE-A-39,24,291 merely as an example, to which reference is expressly made otherwise to explain all terms not presented here in greater detail.

Known biopsy needles have at least one inner needle (mandrel) and an outer tube (also called a cannula). The mandrel has a recess (notch) located in the vicinity of its distal end, provided with a point, said notch receiving the tissue sample to be collected and having at its proximal end a first connecting element for connection with a slide of the biopsy gun. The outer tube or cannula is displaceably guided on the inner needle, and is likewise provided at its proximal end with (a second) connecting element for connection with another slide of the biopsy gun. The connecting elements in known biopsy needles are designed as flanges that cooperate with matching contact surfaces on the slides.

The biopsy needle described in DE-A-39,24,291 is shown in FIGS. 1a–1d and 2.

The inserting unit illustrated in FIGS. 1 and 2 serves to insert biopsy cannulae and includes three slide elements 1 to 3 which are supported in a housing 4 for displacement along a common axis 5. In order to reduce the illustration to the essentials, merely one pin element 6 is shown as one example of the supporting elements on which the slide 1 is supported for displacement along the extension of the axis 5.

Compression springs 7 to 9 are provided to drive the various slides, whereof spring 7 is inserted between the casing 4 and the rear face of the slide 2, while spring 8 is located between a stop 10 at the slide 1 and the bearing surface 2' at the slide 2, whereas spring 9 is clamped between another stop 11 at the slide 1 and the slide 3.

Moreover, pawls 12 to 14 are provided as trigger elements whereof pawl 12 is supported at the casing while the pawls 13 and 14 are provided at the slide 2. The pawls 12 and 14 engage into associated recesses at the slides 2 or 3, respectively, while the pawl 13 bears against the stop 10 of the slide 1.

FIG. 2 illustrates the attachment of a biopsy needle 21 at the slide 2 and of an exterior tube 22 of a biopsy cannula at the slide 3. FIG. 2 shows the provision of a positive connection as an example of the interconnection between the elements 21 and 22 of the biopsy cannula, on the one hand, and the slide elements 2 and 3, on the other hand.

In the initial condition prior to the initiation of the inserting procedure, which is illustrated in FIG. 1a, the compression springs 7 to 8 are biased while the slide elements 1 to 3 are each arrested by the associated pawls or triggering elements 12 to 14. The cannula is retracted accordingly, with the exterior tube 22 covering the cavity in the biopsy needle 21.

The sampling operation is started by actuation of the pawls or triggering elements 12. This action causes the slides 1 to 3 to be jointly displaced by the spring 7 along the axis 5. A stop 41 at the casing 4 limits the distance by which the three slides may be displaced.

FIG. 1b illustrates the condition of the inserting unit after insertion of the biopsy cannula. As a result of the joint movement of the individual cannula elements, the exterior tube 22 remains in a position pushed over the needle 21 so far that the cavity in the needle 22 is covered.

With the elements in this position, it is now possible to actuate the trigger element 14 either automatically under control of appropriate actuator elements such as a (non-illustrated) cam guide at the casing 4 or manually. This operation initiates the movement of the slide 3 under the action of the spring 9 toward the stop 10. FIG. 1c shows the result of this movement for the inserting unit. Retraction of the exterior tube 22 into a position behind the cavity in the biopsy needle is caused by the movement of the slide element 3 relative to the slides 1 and 2.

Then the triggering element 13 is actuated equally automatically, e.g., by means of an appropriate cam guide, or by hand. This action causes the spring 8 to displace the slide 1 together with the slide 3 fixed to it in a direction toward the stop 41 while the slide 2 remains stationary (FIG. 1d). As a result of this movement, the exterior tube 22 is pushed again over the cavity in the needle 21. The advancing movement of the exterior tube 22 separates that part of the tissue from the remaining tissue which has bulged into the cavity due to the elasticity of the tissue, such that a small tissue sample is retained in the cavity, which may then be removed, e.g., by a suitable rearward movement of the inserting unit, with the biopsy cannula following as one unit consisting of the needle 21 and the exterior tube 22.

Known biopsy needles have the disadvantage that under certain conditions it may be difficult to insert the biopsy needle into the biopsy gun under sterile conditions. In known biopsy needles, the mandrel is freely displaceable in the cannula; on the other hand, the two slides of the biopsy gun, with which the connecting elements provided on the mandrel and the cannula must be connected, have a certain spacing that depends upon the state of the biopsy gun (cocked or not cocked). It may therefore be necessary, prior to inserting the biopsy needle, to align the latter relative to the relative position of the mandrel and cannula. In addition, under certain conditions the flange connection does not prevent individual elements from slipping relative to the slide.

SUMMARY OF THE INVENTION

The goal of the invention is to improve a biopsy system and a biopsy needle especially suitable for use in a so-called biopsy gun, in such fashion that no alignment of the individual parts of the biopsy needle relative to one another is required for inserting the biopsy needle into the biopsy gun.

According to the invention, a biopsy system is provided with a biopsy gun and a biopsy needle. In the biopsy system according to the invention, the connecting elements of the inner needle and the outer tube have an opening or a recess for connection with the respective slide, into which recess a pin provided on the respective slide can be inserted. Connecting the biopsy needle and slide by the engagement of pins in recesses and especially in openings, when removing the spacer, prevents inadvertent displacement of the biopsy needle, unlike when flanges are used, both in the direction of the lengthwise axis of the needle and also perpendicularly thereto. In addition, at least one slide has a rib running along the length of the biopsy needle, said rib engaging a recess in the connecting element so that protection is provided against rotation.

The connection between the connecting part connected with the needle and the respective slide is made releasable according to the invention. Of course it is possible with this connecting technique to design the respective connecting parts to be either female or male, in other words the connecting shapes are interchangeable in mirror image fashion. It is merely important that the connecting parts used be designed to match one another.

A spacer is also provided which, prior to the insertion of the biopsy needle into the biopsy gun, is connected with the first and the second connecting elements, and which is removable after the biopsy needle is mounted on the biopsy gun. By virtue of the spacer, the mandrel and cannula are aligned relative to one another in such fashion that the spacing of their connecting elements corresponds to that of the matching receiving elements on the respective slides. It is especially advantageous in this regard that insertion of the biopsy needle into the biopsy gun by the spacer is only possible in a certain state of the biopsy gun. It is preferable for the spacer to be so designed that it permits the biopsy needle to be inserted into the biopsy gun only when the latter is cocked.

An improvement can be provided in which the spacer can be removed after insertion of the biopsy needle into the biopsy gun with the cover of the biopsy gun nearly closed has the advantage that removal of the spacer cannot lead to a loosening of the biopsy needle from its mount on the slide of the biopsy gun. Removal of the spacer with the cover of the biopsy gun nearly closed can be accomplished in particular by each connecting element having at least one lateral projection that engages in a corresponding recess provided on the spacer.

The design of the connecting elements according to the invention also makes it possible for the connecting element of the outer tube to have a Luer lock connection at its proximal end. This makes it possible to introduce or pump away a fluid through the outer tube or cannula. In addition, the connecting element of the inner tube can have a projection on its side facing the distal end, said projection engaging the Luer lock connection so that a certain locking of the mandrel and cannula can be achieved.

A further design has the special advantage that when, for certain reasons, the biopsy needle must be introduced by hand and not with a gun, the stop on the spacer, which is flush with the front surface of the biopsy gun, enables the depth to be monitored when introducing the biopsy needle.

It is advisable for safety reasons to permit the biopsy needle to be fired only when the flap on the biopsy gun is closed. It is also provided for different firing depths of the biopsy needle such as 15 mm, 22 mm, and 32 mm for example, to be provided and for the respective firing depths used to be displayed graphically on the biopsy system by various graphics or colors for example.

The various firing depths can be achieved for example by using plug devices that block the movement of the biopsy needle after it has traveled a specific distance. Since the biopsy needle is connected with the respective slide, it is also possible for the movement of the slide to be restricted after a given distance.

BRIEF DESCRIPTION OF THE DRAWINGS

The invention will now be described with embodiments and with reference to the drawing without limitation of the general idea of the invention, to which drawing all details according to the invention not described more specifically in the text are referred to relative to disclosure.

DETAILED DESCRIPTION OF THE PREFERRED EMBODIMENTS

Figure 1A:
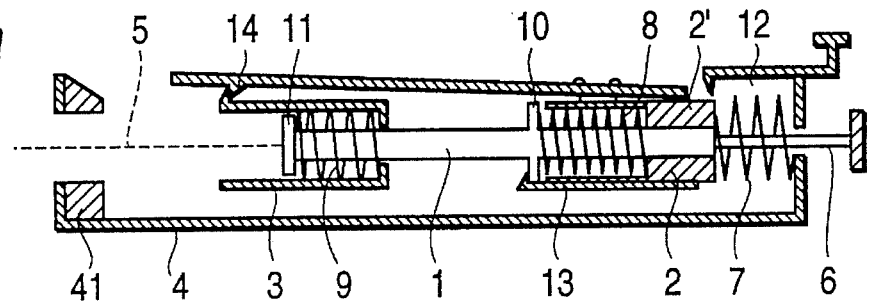
FIGS. 1a–1d show schematic section views through a known inserting unit in its various operating conditions.
Figure 1B:
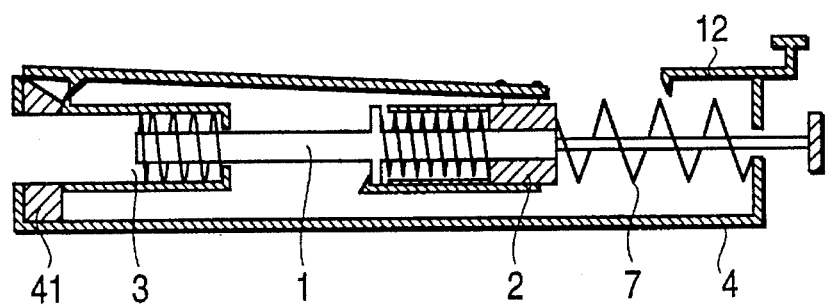
Figure 1C:
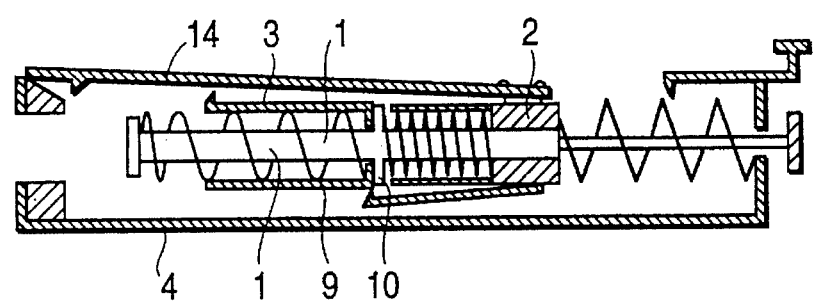
Figure 1D:
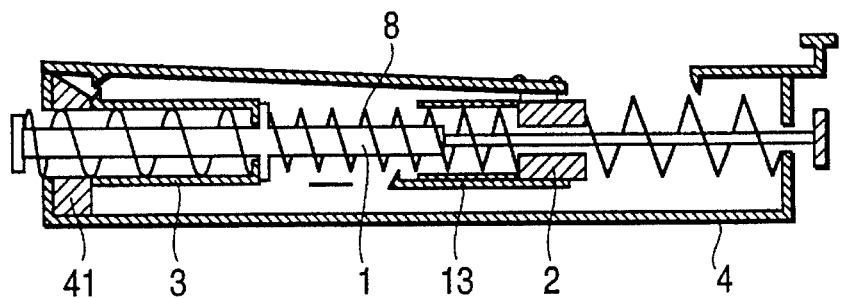
Figure 2:
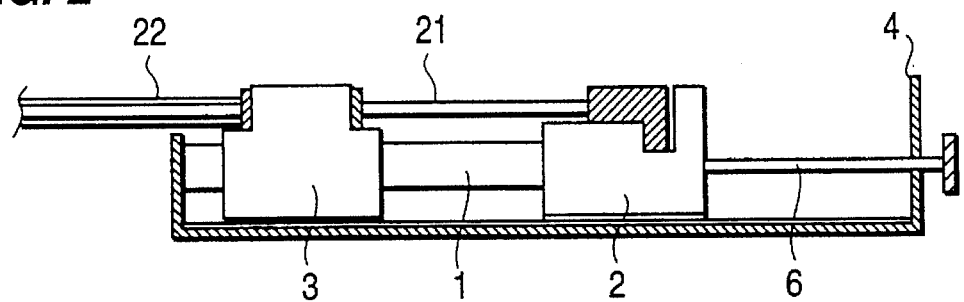
FIG. 2 illustrates the attachment of a biopsy cannula at a known inserting unit according to FIGS. 1a–1d.
Figure 3:
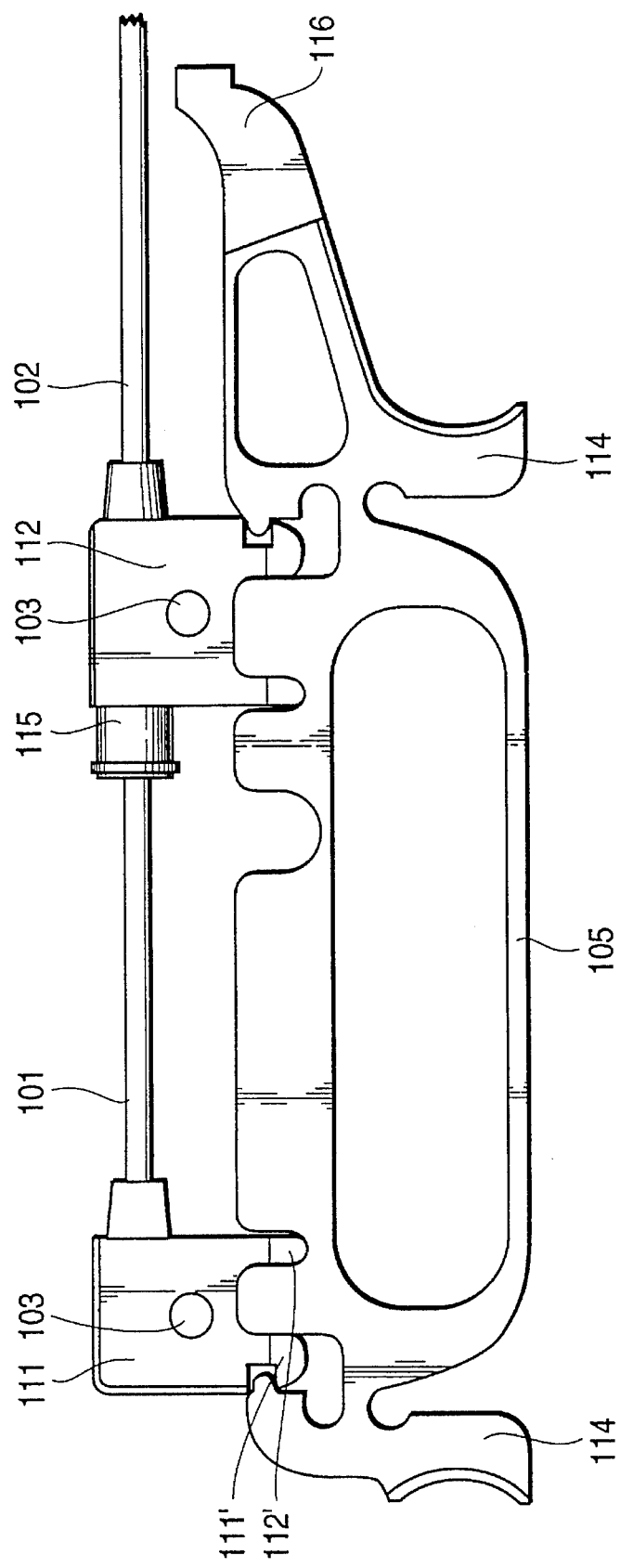
FIG. 3 is a side view of a biopsy needle according to the invention.
Figure 4:
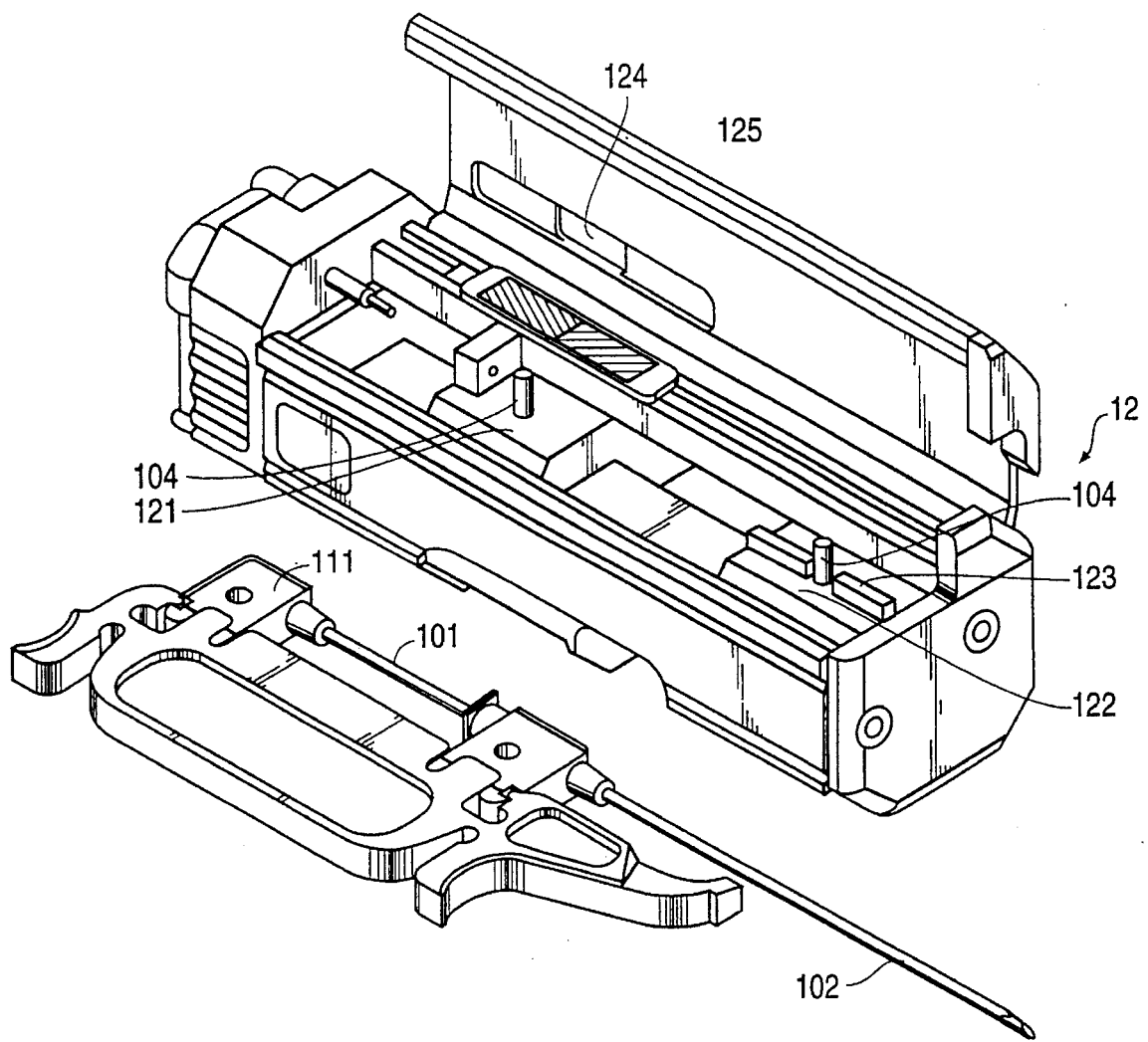
FIG. 4 is a perspective view of a biopsy system according to the invention.

FIG. 3 shows the proximal area of a biopsy needle, especially suited for use in a so-called biopsy gun 120 (see FIG. 4). The biopsy needle has an inner needle 101, also called a mandrel, and an outer tube 102 (cannula) displaceably guided on inner needle 101.

Mandrel 101 has a recess in the vicinity of its distal end (shown in FIG. 4) which receives the tissue sample to be collected, and has a first connecting element 117 at its proximal end for connection with a slide 121 (FIG. 4) of the biopsy gun. Cannula 102 also has a connecting element 112 at its proximal end for connection with another slide 122 of the biopsy gun. Connecting elements 111 and 112 each have an opening 103, into which a pin 104 provided on the respective slide 121 or 122 can be inserted. In addition, slide 122 has a rib 123 that extends in the lengthwise direction of the biopsy needle, said rib engaging a recess (not shown in the Figures) in the corresponding connecting element 112.

According to the invention, a spacer 5 is provided connected with the first and second connecting elements 111 and 112, and removable following insertion of the biopsy needle into biopsy gun 120. The spacer in particular is designed so that it allows the biopsy needle to be inserted into the biopsy gun only when the latter is cocked. In addition, spacer 105 can be removed after the biopsy needle has been inserted into the biopsy gun with lid 106 of the biopsy gun nearly closed.

To connect spacer 5 and the biopsy needle, each connecting element 111 or 112 has two lateral projections 111' and 112', one of which has a nose that abuts a nose with a complementary design on the corresponding recess in the spacer. The nose at each recess is provided on an elastic part 114 of the spacer, movable by associated finger contact surfaces.

In addition, connecting element 112 of outer tube 112 has a Luer lock connection 115 at its proximal end, into which a projection on connecting element 111 of the inner tube or of mandrel 101 can engage.

In addition, spacer 105 has a stop 116 flush with the front surface of the biopsy gun.

The spacer is preferably made as an injection-molded part from a plastic material.

The biopsy gun shown in FIG. 4 allows the device to be cocked in two movement phases. During the first cocking process, slide 122 of cannula 102 is brought into the cocking position and the notch of mandrel 101 is opened. In the second cocking process, slide 121 of mandrel 101 is brought into its cocked position. This cocking process also permits simple removal of the tissue sample from the "notch".

The gun also has a switchable firing depth, namely 122 and 115 mm and 32 and 22 mm. When the device is cocked, the trigger is automatically secured and must then be deliberately released.

A cutout 124 in lid 106 shows the loaded state of the biopsy gun by means of a color marking 125:

Green/green=totally released, green/red=cannula in cocked position, red/red=cannula and mandrel cocked.

I claim:

1. A biopsy system for collecting a tissue sample, comprising a biopsy needle and a biopsy gun into which said biopsy needle is insertable, said biopsy gun comprising a housing and first and second slides, each of said first and second slides having a pin provided thereon, said biopsy needle comprising an inner needle having a recess in a vicinity of a distal end thereof for receiving the tissue sample and having a first connecting element at a proximal end thereof, and an outer tube displaceably guided on said inner needle and having a second connecting element at a proximal end thereof, wherein each of the first and second connecting elements has a hole therein into which a respective pin on each of said first and second slides is insertable, and wherein at least one of said slides has a rib running in a lengthwise direction of said biopsy needle, said rib being capable of engaging a recess provided in a respective one of said first and second connecting elements.

2. Biopsy system according to claim 1 characterized in that a spacer is provided for the biopsy needle, said spacer being connected with the first and second connecting elements and removable following insertion of the biopsy needle into the biopsy gun.

3. Biopsy system according to claim 2 characterized in that the spacer permits the biopsy needle to be inserted into the biopsy gun only when the latter is cocked.

4. Biopsy system according to claim 2 characterized in that the spacer is removable following insertion of the biopsy needle into the biopsy gun with a lid of the biopsy gun nearly closed.

5. Biopsy system according to claim 2 characterized in that each of said first and second connecting elements has at least one lateral projection which engages a corresponding recess provided on the spacer.

6. Biopsy system according to claim 5 characterized in that each of said first and second connecting elements has two lateral projections, one of which has a nose that abuts a nose of complementary design and the corresponding recess.

7. Biopsy system according to claim 6 characterized in that the nose at each recess is provided on an elastic part of the spacer and in that the elastic parts are movable by associated finger contact surfaces.

8. Biopsy system according to claim 1 characterized in that the second connecting element has a Luer lock connection on its proximal end.

9. Biopsy system according to claim 8 characterized in that the first connecting element has a projection on its side facing the distal end, said projection engaging the Luer lock connection.

10. Biopsy system according to claim 2 characterized in that the spacer has a stop that is flush with a front surface of the biopsy gun.

11. Biopsy system according to claim 1 characterized in that initially the slide of the outer tube and then the slide of the inner needle is brought into a cocked position during cocking.

12. Biopsy system according to claim 1 further comprising a window provided in the housing for displaying a loaded state of the biopsy system.

13. Biopsy system according to claim 1 characterized in that the biopsy gun is operable only with a lid thereof closed and therefore the biopsy needle penetrates the tissue only when the lid is closed.

14. Biopsy system according to claim 1 characterized in that a firing depth of the biopsy needle can be adjusted for at least two depth ranges.

* * * * *